US008763559B2

(12) United States Patent
Salzmann et al.

(10) Patent No.: US 8,763,559 B2
(45) Date of Patent: Jul. 1, 2014

(54) WIRELESS MONITORING OF LABORATORY ANIMALS

(71) Applicant: Vertex Pharmaceuticals, Inc., Cambridge, MA (US)

(72) Inventors: Philip Salzmann, Cardiff, CA (US); Trang Nguyen, Gurnee, IL (US); James Sinclair, Carlsbad, CA (US)

(73) Assignee: Vertex Pharmaceuticals, Incorporated, Cambridge, MA (US)

( * ) Notice: Subject to any disclaimer, the term of this patent is extended or adjusted under 35 U.S.C. 154(b) by 0 days.

(21) Appl. No.: 13/777,239

(22) Filed: Feb. 26, 2013

(65) Prior Publication Data

US 2013/0176035 A1    Jul. 11, 2013

Related U.S. Application Data

(63) Continuation of application No. 12/577,679, filed on Oct. 12, 2009, now Pat. No. 8,468,975.

(51) Int. Cl.
*A01K 1/03* (2006.01)

(52) U.S. Cl.
USPC ......................................................... 119/421

(58) Field of Classification Search
USPC ......................................................... 119/421
See application file for complete search history.

(56) References Cited

U.S. PATENT DOCUMENTS

| | | | |
|---|---|---|---|
| 3,304,911 A * | 2/1967 | Hakata et al. ................ | 119/421 |
| 3,602,806 A | 8/1971 | Czekjewski et al. | |
| 3,656,456 A * | 4/1972 | Stigmark et al. ............. | 119/421 |
| 3,803,571 A | 4/1974 | Luz | |
| 3,823,990 A | 7/1974 | Gilinson, Jr. | |
| 4,337,726 A * | 7/1982 | Czekajewski et al. ........ | 119/421 |
| 4,634,975 A | 1/1987 | Eccleston et al. | |
| 4,918,432 A | 4/1990 | Pauley et al. | |
| 4,968,974 A * | 11/1990 | Sakano ....................... | 340/573.3 |
| 5,680,106 A | 10/1997 | Schrott et al. | |
| 5,831,527 A | 11/1998 | Jones, II et al. | |
| 5,838,233 A | 11/1998 | Hawes et al. | |
| 5,951,362 A | 9/1999 | Siu | |
| 6,095,092 A | 8/2000 | Chou | |
| 6,404,340 B1 | 6/2002 | Paradiso et al. | |
| 6,637,372 B2 * | 10/2003 | Mauderli et al. .............. | 119/417 |
| 6,644,244 B2 * | 11/2003 | Mauderli et al. .............. | 119/417 |
| 6,834,251 B1 | 12/2004 | Fletcher | |
| 6,837,184 B2 * | 1/2005 | Gondhalekar et al. ........ | 119/421 |
| 6,891,469 B2 * | 5/2005 | Engellenner .................. | 340/505 |

(Continued)

FOREIGN PATENT DOCUMENTS

GB             556607         10/1943

OTHER PUBLICATIONS

PCT International Search Report and Written Opinion mailed Dec. 16, 2010 in PCT Application No. PCY/US2010/050732, filed Sep. 29, 2010.

*Primary Examiner* — Kristen C Hayes
(74) *Attorney, Agent, or Firm* — Knobbe Martens Olson & Bear LLP

(57) ABSTRACT

Systems and methods for monitoring laboratory animals includes a tag comprising an inductive element and a capacitive element attached to a portion of a laboratory animal. The position of the portion is detected by monitoring the effect of the tag on a time-varying magnetic field having different frequencies, one near tag resonance, and one away from tag resonance.

10 Claims, 6 Drawing Sheets

(56) References Cited

U.S. PATENT DOCUMENTS

| | | |
|---|---|---|
| 6,969,987 B2 | 11/2005 | Schwartzbart |
| 6,972,677 B2 | 12/2005 | Coulthard |
| 7,389,744 B2 * | 6/2008 | Zhang et al. .................. 119/421 |
| 7,902,971 B2 * | 3/2011 | Engellenner .................. 340/505 |
| 8,468,975 B2 * | 6/2013 | Salzmann et al. ............ 119/421 |
| 2001/0038332 A1 | 11/2001 | Rodgers et al. |
| 2002/0130775 A1 * | 9/2002 | Engellenner .................. 340/540 |
| 2002/0135479 A1 | 9/2002 | Belcher et al. |
| 2003/0200814 A1 | 10/2003 | Oh et al. |
| 2004/0001002 A1 | 1/2004 | Blum et al. |
| 2004/0203361 A1 | 10/2004 | Belcher et al. |
| 2007/0080805 A1 | 4/2007 | Franklin et al. |
| 2007/0107666 A1 * | 5/2007 | Salzmann et al. ............ 119/421 |

* cited by examiner

WIRELESS MONITORING OF LABORATORY ANIMALS

CROSS-REFERENCE TO RELATED APPLICATIONS

This application claims priority to and is a continuation application of U.S. application Ser. No. 12/577,679, filed Oct. 12, 2009. Any and all priority claims identified in the Application Data Sheet, or any correction thereto, are hereby incorporated by reference under 37 CFR 1.57.

BACKGROUND

1. Field of the Invention

The invention relates to wireless monitoring of laboratory animals. In some aspects, the invention relates to detection and evaluation of paw guarding.

2. Description of the Related Art

In the discovery of neurological drugs, e.g., analgesics, many animal pain models are used. Most animal models used to screen for novel analgesics are based on monitoring the animal's response to evoked pain, often following an injury or insult. A typical example is the CFA model where a complete Freund's adjuvant (CFA) is injected into the rear paw of a rat to cause inflammation (i.e., injury). A stylus fitted with a strain gauge is then used to poke the injured paw and the force at which the animal withdraws its paw is taken as a measure of pain (i.e., evoked pain). Evoked pain models suffer from at least three disadvantages. First, the experiment is tedious as a lab technician has to wait for the animal to settle down before the stimulus can be reliably applied. Second, objectivity cannot be guaranteed. Even under blinded conditions, the temptation for a technician to bias results is always present. Lastly, pain evoked by an external stimulus is not representative of what humans typically feel when they are in pain. Indeed, human pain is mostly non-evoked: subsequent to injuries, humans continuously feel pain without any external stimulus (spontaneous pain).

Thus, there is a need for a spontaneous pain model and the corresponding animal pain detectors.

SUMMARY OF CERTAIN EMBODIMENTS

In one embodiment, the invention comprises a system for detecting the position of a paw on a rodent. The system comprises at least one coil, and a resonant circuit attached to a laboratory animal. The resonant circuit may define a resonant frequency. The system also comprises a signal generator electrically coupled to the at least one coil and configured to drive the at least one coil with at least a first drive signal comprising a first frequency and a second drive signal comprising a second frequency, wherein the second frequency is more distant from the resonant frequency than the first frequency. Further provided is a detection circuit coupled to the at least one coil and configured to detect an impedance change in the at least one coil between application of the first frequency to the at least one coil and application of the second frequency to the at least one coil, and to generate an output signal representative of resonant circuit position with respect to the at least one coil based at least in part on the impedance change.

Methods of detecting the position of a portion of a laboratory animal is also provided. The method may comprise attaching a resonant circuit to the animal, placing the animal proximate to at least one coil, driving the at least one coil with a signal of at least a first frequency and a second frequency; and detecting an impedance change in the at least one coil between the first and second frequencies. The method may be applied to the monitoring of a variety of laboratory animal behaviors. In some advantageous embodiments, methods of monitoring paw guarding are provided. These methods have advantageous application to methods of assaying an antinociceptive drug candidate.

In another embodiment, a cage for holding and monitoring a laboratory animal comprises a first coil positioned below a floor of the cage and a second coil positioned above the floor of the cage. In advantageous embodiments the first coil, the second coil, and the floor may be substantially aligned along a common longitudinal axis, and the floor may be positioned at approximately midway between the first coil and the second coil.

DETAILED DESCRIPTION OF CERTAIN EMBODIMENTS

Figure 1:
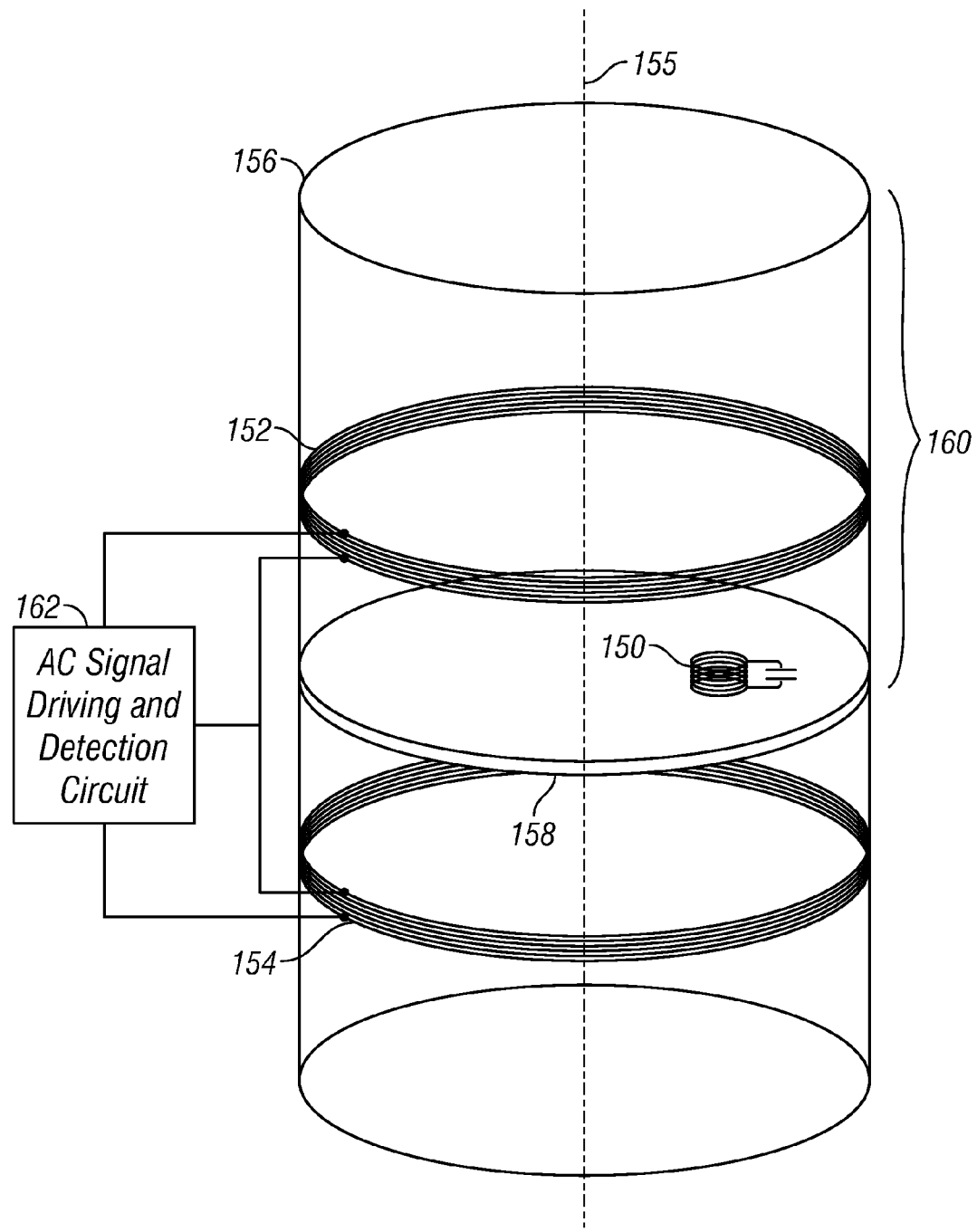
FIG. 1 depicts one system for detecting the position of a tag.

The following detailed description of certain embodiments presents various descriptions of specific embodiments of the invention. However, the invention can be embodied in a multitude of different ways as defined and covered by the claims. In this description, reference is made to the drawings wherein like parts are designated with like numerals throughout.

The terminology used in the description presented herein is not intended to be interpreted in any limited or restrictive manner, simply because it is being utilized in conjunction with a detailed description of certain specific embodiments of the invention. Furthermore, embodiments of the invention may include several novel features, no single one of which is solely responsible for its desirable attributes or which is essential to practicing the inventions herein described.

Laboratory animals such as rodents treated with CFA in their paws, or other pain-inducing procedures, have been seen to "guard" their injured paws. Guarding refers to the fact that the injured animal tends to keep its weight off the affected paw by lifting it a short distance above the cage floor so that no weight is applied when standing or moving. As this behavior is not elicited by any external stimulus, this behavior can be viewed as representative of some spontaneous pain felt by the animal. Although paw guarding has been observed, it has not been quantified, especially not in an automated way, in a manner that allows its use as a model for analysis of analgesic effectiveness. Certain embodiments as will be described relate to systems and methods for electronically detecting this paw elevation so that spontaneous pain can be accessed in an impartial way.

In some embodiments, systems and methods are provided for detecting the position of a tag. In one advantageous embodiment, the tag is attached to a paw of a rodent such as a rat, although as will be described further below, the tag may be affixed to any part of any type of laboratory animal. The tag may be attached to the animal using any suitable structure. In one embodiment, adhesive is used to attach the tag to a rodent's paw. In some advantageous embodiments, the tag does not need to have a power source and may be used as a wireless device. In one embodiment, the tag comprises an inductive element and a capacitive element. Any electrical structures may be used for the inductive and capacitive elements provided the electrical structures exhibit corresponding inductive and capacitive behavior. In one embodiment, the inductive element is an inductor formed as a metal coil and the capacitive element is a capacitor formed as adjacent parallel metal plates. In one embodiment, the inductor and capacitor are connected in parallel, forming a resonant LC circuit.

The position of such a resonant LC circuit can be determined by placing the LC circuit in a time-varying magnetic field established inside and around a coil as the coil is driven by AC signals such as a sinusoidal voltage of some frequency $\omega$. When an LC circuit is placed within or otherwise near the coil, it alters the magnetic field generated by the coil and changes the coil's impedance. The impedance change is dependent on the resonant frequency of the resonant circuit and the position of the resonant circuit with respect to the coil. Detection of this impedance change can provide an indication of the position of the LC circuit. Accordingly, in one embodiment, a system for detecting the position of a tag is provided that includes at least one coil, and a tag including an inductive element and a capacitive element. The tag is attached to a portion of a laboratory animal, such as the injured paw of a rodent which is placed near the AC driven coil. As the rodent moves its tagged paw, the coil impedance varies. The system may be used to detect a change in the impedance of the coil so as to detect spontaneous pain in the injured paw of the rodent.

FIG. 1 depicts one system for detecting the position of a tag. The system includes a tag 150 comprising an inductor and capacitor connected in parallel. The system also includes two coils 152 and 154. In one embodiment the coils 152 and 154 are wired in series. In one embodiment, the coils 152 and 154 are wound on a cylindrical tube 156 one above the other, aligned along a longitudinal axis 155 of the tube 156. A floor 158 is installed, preferably at or near the midpoint between the two coils and also aligned along the longitudinal axis 155. The space above the floor 158 constitutes the cage 160 in which the animal is confined during the experiment. The coils 152 and 154 are connected to an AC signal driving and detection circuit 162.

The AC signal generator 164 sets up an alternating current through the coils 152 and 154, which induces a time-varying magnetic field in and around each coil. In one embodiment, the coils 152 and 154 are driven by an AC signal whose frequency (e.g., 0.5-1 MHz) is chosen to be close to or equal to the resonant frequency of the inductor-capacitor element in the tag 150. Because the drive frequency is chosen to be approximately equal to this resonant frequency, the inductor-capacitor element is very efficient at removing energy from the sensing field. Thus, when the tag 150 is introduced into the coils' time-varying magnetic field, the inductor-capacitor circuit absorbs some of the field's energy and changes the coils' impedance. This impedance change can be sensed with the proper detection circuit 162 connected to the coils 152 and 154. The impedance change can be used to indicate the position of the tag 150 within the time-varying magnetic field induced by coils 152 and 154.

In another embodiment, the system may include only one coil. The system detects the impedance change of the one coil caused by any positional change of the tag 150. In certain applications, the two-coil arrangement as shown in FIG. 1 offers benefits over the one-coil alternative. When used to detect spontaneous pain in the injured paw of a rodent, the system should detect only vertical motions of the tag 150 as horizontal motions of the injured paw do not indicate spontaneous pain. In a one-coil system, as the magnetic field in its vicinity is not completely homogeneous spatially due to edge effects, a change in coil impedance still ensues when the animal moves laterally without lifting its tagged paw.

In the two-coil arrangement of FIG. 1, the field in the volume between the two coils 152 and 154 is quite homogeneous. As the tag 150 is moved upward from the cage floor 158, both coils 152 and 154 experience a change in impedance. More energy is extracted from the upper coil 152 while less is drawn from the lower one 154. Since the field has almost no radial component, lateral movements of the tag 150 have little effect. In the exemplary embodiment, the cage floor 158 is placed at approximately the midpoint between the two coils so that when the rodent puts its foot down (see FIG. 4 described below, for example), both coils are affected to the same extent by the tag 150. In one embodiment, the system may be adjusted so that, when the rodent puts its paw on the floor, the signal is close to zero.

Figure 2:
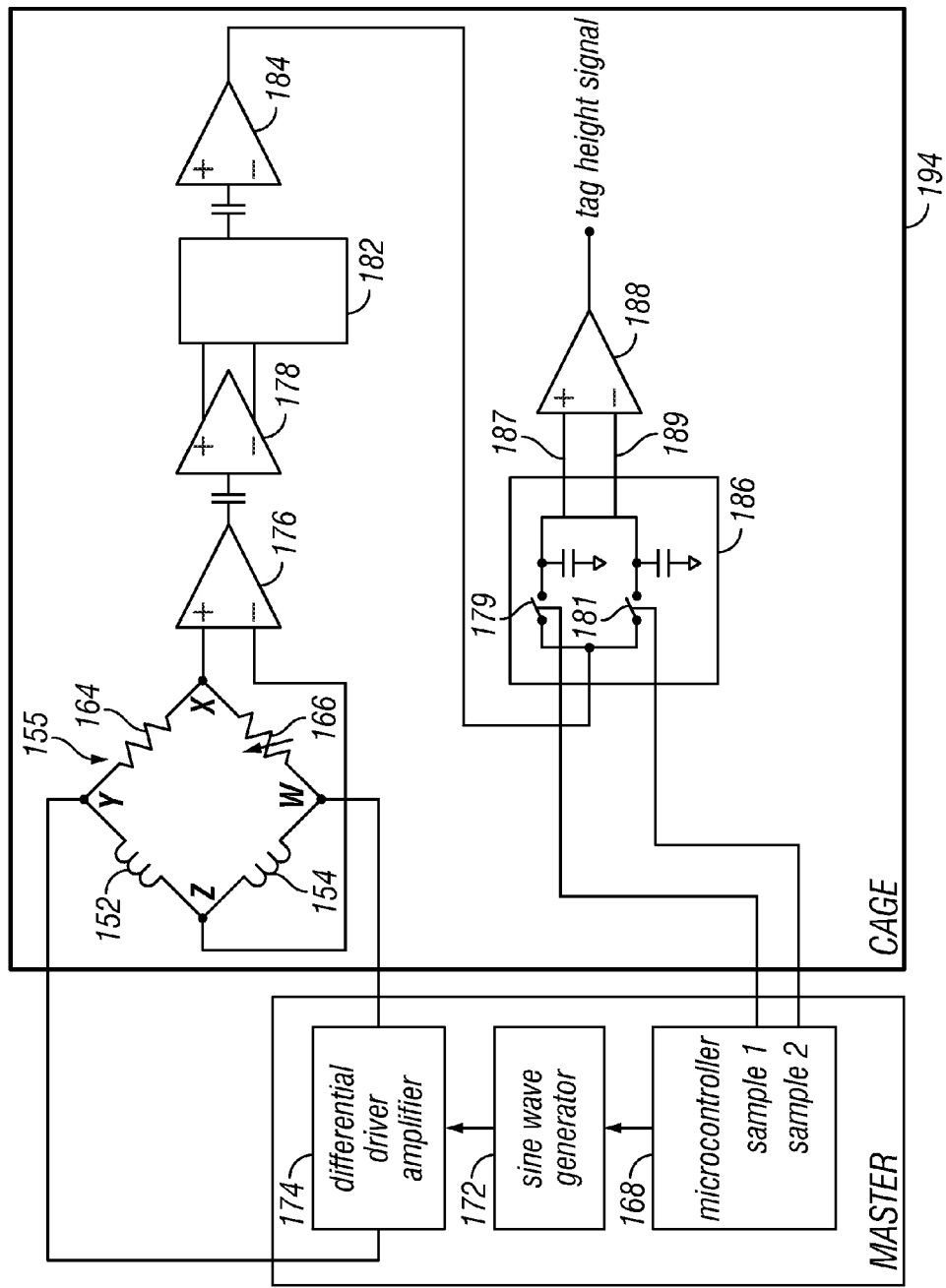
FIG. 2 illustrates one embodiment of a AC signal driving and detection circuit.

FIG. 2 illustrates one embodiment of a time varying signal driving circuit 192 and impedance change detection circuit 194. The impedance difference between the two coils 152 and 154 is measured with a Wheatstone bridge 155 as shown in FIG. 2. The coils 152 and 154 form two legs of the Wheatstone bridge 155. The coil 152 is connected to the bridge 155 at nodes Y and Z. The coil 154 is connected to the bridge 155 at nodes W and Z. The bridge 155 further includes two resistors 164 and 166. In one embodiment, the resistor 164 is fixed and the resistor 166 is adjustable.

In one embodiment, to maximize energy input, the bridge is driven by two AC signals, such as sinusoidal signals, that are 180° out of phase with each other. If the bridge is perfectly balanced, there is no signal at its outputs X and Z while any imbalance results in a sinusoidal voltage between these two points at the drive frequency. This imbalanced signal is amplified by an amplifier 176 whose output is AC-coupled via a capacitor to an amplifier 178. The AC output of the amplifier 178 is run through an envelope detector 182 to obtain the amplitude of the signal. The envelop detector 182 is an electronic circuit that takes a high-frequency signal as input, and provides an output which is representative of the zero-peak or peak-peak amplitude of the original AC signal over multiple AC cycles. The amplitude output from the envelop detector 182 is AC-coupled to the amplifier 184 via a capacitor.

In certain applications, the AC coupling between amplifiers in this cascade is beneficial because, given the amplifier gains involved, any small DC offset would cause saturation. However, because of this AC coupling, the output of the amplifier 184 only includes signals indicative of a change in the coils' impedance. In other words, every time the tag 150 is moved vertically, a voltage appears at the output of the amplifier 184 but it quickly decays to zero. The output of the amplifier 184 does not provide a DC voltage that is representative of the static value of the coils' impedance characteristics in the absence of changes in tag position and/or drive frequency. As explained further below, rather than attempting to produce a tag position measurement by measuring coil impedance as a function of tag position directly, advantageous embodiments of the invention measure coil impedance as a function of coil input drive signal frequency. By switching between or sweeping through multiple frequencies, tag position relative to the floor can be deduced without the detection difficulties associated with detecting position using steady state DC coupled measurements performed at a single frequency.

In the exemplary embodiment, the Wheatstone bridge 155 is excited with AC signals with its frequency varying with time in a range including a frequency at the resonance of the tag 150. The output of the amplifier 184 is now a varying signal reaching a maximum value at the resonance frequency and falling off as the frequency of the AC signals move away from the resonance frequency. The resonant maximum reflects the coils impedance imbalance at the resonant frequency and hence the LC tag's vertical position. By comparing the resonant maximum to an off-resonance minimum, a signal can be obtained that is proportional to the coils' impedance imbalance, which is related to the LC tag's vertical position.

In the exemplary embodiment, a sine wave generator 172 controlled by a microcontroller 168 repeatedly outputs a frequency sweep (e.g., from 460 KHz to 620 KHz). A differential driver amplifier 174 amplifies the frequency sweep from the sine wave generator 172 and then excites the Wheatstone bridge 155 with the amplified signal. A dual sample-and-hold circuit 186 is configured to sample the output of the amplifier 184 at two points during each frequency sweep. In one embodiment, the samples are taken once at the resonant frequency where this output reaches the maximum (e.g. switch 179 is momentarily closed at this point in the sweep) and once far away from the resonance where it reaches the minimum (e.g. switch 181 is momentarily closed at this point in the sweep). A variety of designs for such a sample and hold circuit are well known to those of skill in the art. Functionally, the output of the sample and hold circuit 186 at node 187 is held at the last output of amplifier 184 when the frequency was at or near the LC circuit resonance, and the output of the sample and hold circuit 186 at node 189 is held at the output of amplifier 184 when the frequency was far from the LC circuit resonance. The difference between these two values is amplified by the amplifier 188 whose output is a DC voltage that is related to the LC tag's vertical position relative to the floor of the cage. This DC voltage may be referred to as the tag height signal.

Figure 3:
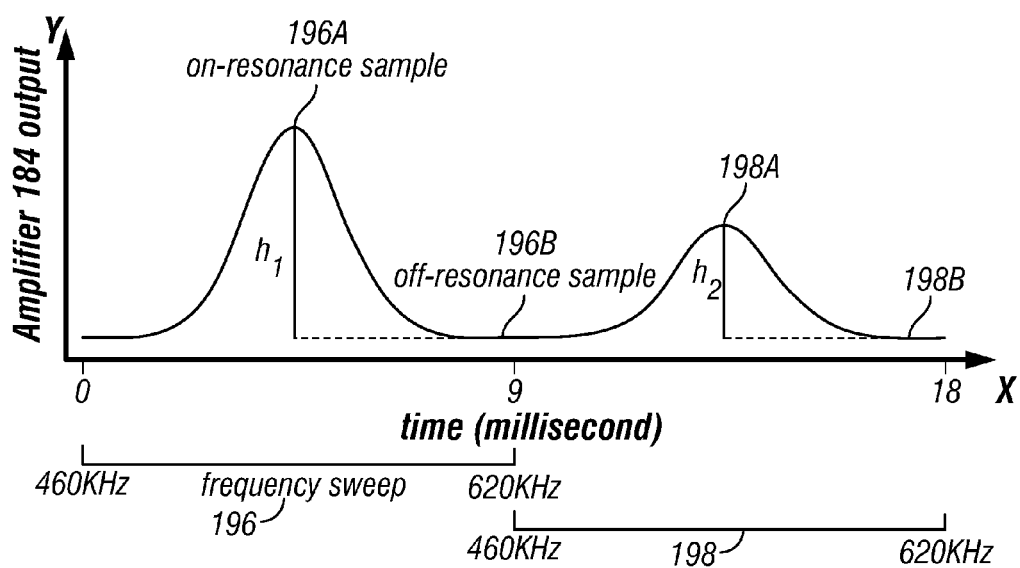
FIG. 3 is a diagram of an exemplary output of the amplifier 184 shown in FIG. 2.

FIG. 3 is a graph of the amplifier 184 output schematically showing the above method. The x axis represents time and the y axis represents the output signal of the amplifier 184. The graph illustrates two cycles of frequency sweeps 196 and 198. During the first frequency sweep 196, an on-resonance sample 196A is sampled at the resonance frequency and an off-resonance sample 196B is taken. The difference between the two samples is h1. Similarly, the difference between the on-resonance sample 198A and the off-resonance sample 198B is h2 during the second frequency sweep 198. The output of amplifier 188 will be h1 after the first sweep, and will be h2 after the second sweep. In this example, the LC tag 150 is closer to cage floor during the second sweep than it is during the first sweep. The measurements detect this position difference as h1 is larger than h2.

In the exemplary embodiment of FIG. 2, the response time of the device is determined by how fast a frequency sweep through the frequency range is performed. In one embodiment that has been found suitable, the frequency sweep takes about 9 milliseconds. Depending on the application, the frequency sweep may be configured to be performed faster or slower.

In one example, the device may, for example, have a sensitivity of about 63 mV/mm with a noise level of about 35 mV. This meets the requirements for monitoring the elevation of an injured paw of a rodent. Typically, it has been found that CFA treated rats guard their injured paws by lifting them about 3 mm above the cage floor. This gives a signal of about 200 mV and a signal-to-noise ratio of about 6.

In another embodiment, a different sampling method may be used to provide a faster response. Instead of a smooth frequency sweep, the AC signals used to drive the bridge 155 can quickly switch between two discrete frequencies, one at resonance and one far away from the resonance. The AC signals stay at each frequency long enough for the envelope detector 182 to provide a reliable output.

It will be appreciated that although the detection circuit of FIG. 2 is illustrated as analog amplifiers and other functional blocks, many of the features of the detection circuit may be implemented digitally with the various signals processed with digital signal processing techniques to produce corresponding measurement values.

The exemplary embodiment may be modified to monitor more than one tag at the same time. In one embodiment, two tags of different resonant frequencies are used. The frequency sweep is performed throughout a frequency range including the resonance frequencies of both tags. As a result, the output of the amplifier 184 has two resonant peaks. The device may sample at three frequency values, once at each resonance and once off resonance, and thus provide two independent tag heights. Following this principle, it is possible to expand this method to detect multiple LC tags provided their resonant frequencies are different enough from each other. Accordingly, the device may track paw elevations from two or more rats that are kept in the same cage.

In some applications, it is desirable to perform testing simultaneously on multiple test subjects, usually four or eight. The device 162 of FIG. 3 includes a master portion 192 and a cage portion 194. The master portion 192 may be able to drive multiple cages each with a cage portion 194. It will be appreciated the circuitry associated with the cage portion 194 may be but need not all be physically attached to its respective cage. All cages thus operate in synchrony as they all subject to the same frequency sweeps simultaneously. When multiple LC tags are used, they differ slightly in their resonant frequencies. At the same time, these LC tags should have their resonant frequencies be within the frequency range and the slight variations in the resonant peak position can be easily accommodated. In the typical range of tag motion observed when the system is used to detect paw guarding, e.g., about 3 mm movement of the injured paw above the cage floor, no appreciable cross talk between the cages has been detected. It has been found that appreciable interference with the measurements due to cross talk requires the tag to be lifted by more than about 10 cm above the cage floor, which is a range of motion not achievable by any rodents.

Figure 4:
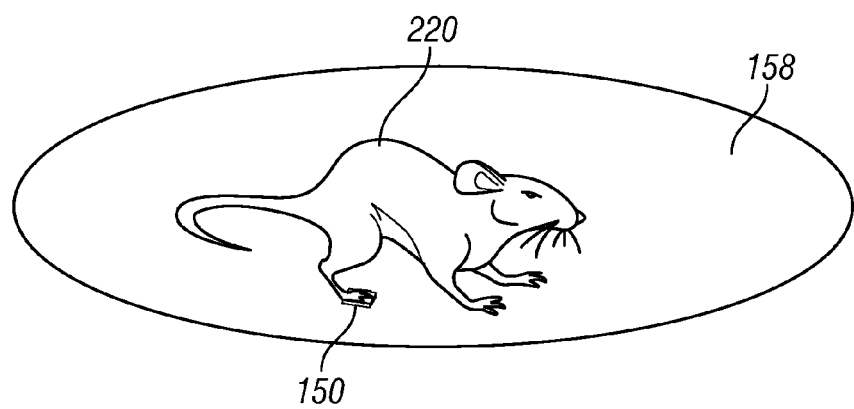
FIG. 4 illustrates a rodent wearing a tag and placed on a floor.

FIG. 4 depicts a rodent 220 placed on the cage floor 158. The tag 150 comprising the inductor-capacitor element may be placed on a hind paw of the rodent 220. In one embodiment, cyano-acrylate glue is used to mount the tag on the bottom of a rodent's paw. When the rodent's leg moves up and down, the tag 150 will also move up and down, inducing a change in the impedance of the coils 152 and 154 (not shown in FIG. 4).

In one embodiment, the tag 150 is designed to satisfy one or more of the following three requirements. First, the tag should be as un-intrusive as possible so as not to cause unintended sensory stimuli to the rat. Second, the tag preferably draws as much energy from the coils' magnetic field as possible. As a result, the tag's quality factor is maximized. Third, the tag should be low cost and easy to clean. The tags may be sonicated in a beaker of acetone immersed in a water bath after use. Preferably, the tags should stand up to this treatment many times.

Figure 5:
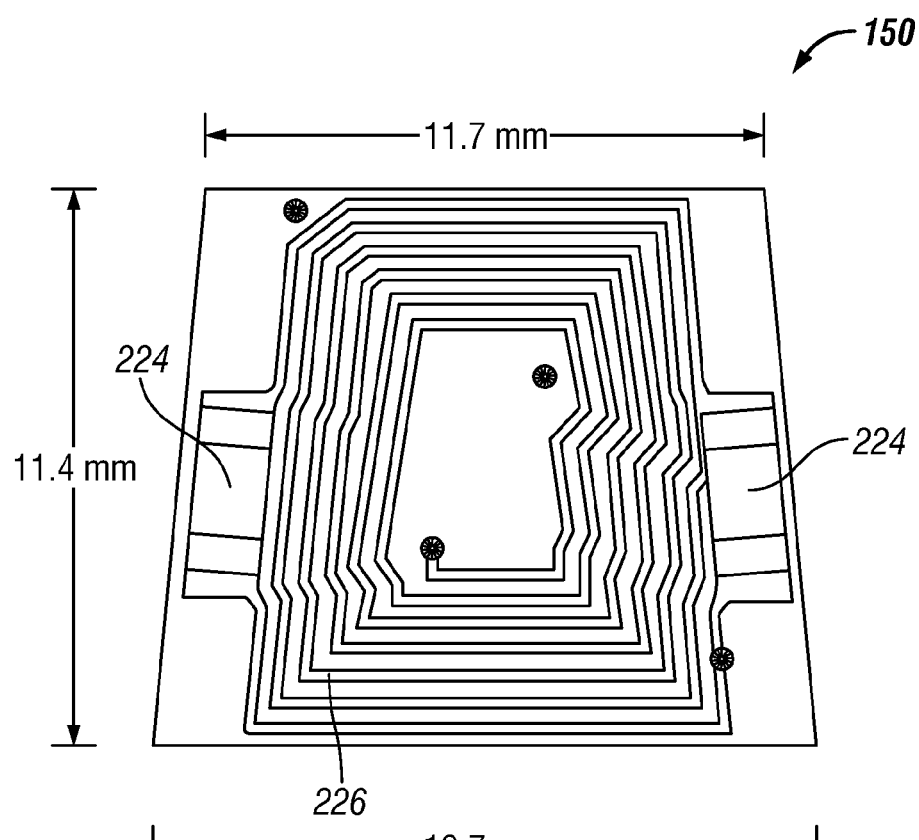
FIG. 5 is a diagram illustrating one embodiment of the LC tag.

In one embodiment, the LC tag 150 is fabricated using multi-layered printed circuit board (PC board) technology. Each tag is a 4-layer PC board in the shape of a small trapezoid. Four spiral traces, one per layer, are connected together to provide an inductance of about 5 mH. The traces' thickness is maximized in order to keep the resistance at a minimum. The circuit further includes two surface mount capacitors (15 nF) of low internal resistance. FIG. 5 is a diagram illustrating the top trace 226 of the inductor and two surface mount capacitors 224. With this design, the LC tag has a quality factor of about 30. In one example, the tag has a resonance frequency of about 560 KHz, a weight of about 0.25 g, and a thickness of about 0.6 mm. Within the short time (e.g., typically 5 minutes) needed to carry out a CFA experiment, the tag has no appreciable effect on the rat's behavior. When a tag is affixed to an uninjured animal, its behavior seems unaffected within this time window. This design works well for this application also because when the printed circuit board is attached to a foot as shown in FIG. 4, the plane of the inductor on the printed circuit board remains substantially perpendicular to the field lines produced in the cage by the coils 152, 154 even when the foot moves up and down. This results in maximum signal without significant variations caused by a changing orientation of the plane of the inductor.

In some embodiments, the detecting apparatus and methods disclosed herein have several advantages when compared with other systems. First, an inductor-capacitor element is very efficient at coupling to a resonant magnetic field, thus generating a large signal. Other structures in a typical laboratory environment are unlikely to be as efficient in coupling to the generated magnetic field. Thus, the chance of detecting extraneous signals is reduced. Second, given the resonant nature of an inductor-capacitor circuit, high levels of amplification are not needed because the signal is fairly large. Thus, the system's sensitivity to interference from stray magnetic fields in the environment is reduced. Third, inductor-capacitor elements can easily be miniaturized using surface-mount components. For example, tags may be made to weigh very little (e.g., 0.3 grams). Thus, a rodent wearing the tag will not perceive significant inertia caused by the tag, which could interfere with its paw movement. Fourth, several coils can function very close to each other without causing cross-interference. It was observed that two coils operating at the same frequency did not interfere with each other even when placed only a few inches apart. While not being bound by any particular theory, it is believed that coil-coil crosstalk is reduced because the amplification level in each coil is not very high. It is believed that coil-tag crosstalk is reduced because the tags only capture a very small area of the field of a coil when not inside the circle of the coil. Accordingly, a large number of units may be deployed close to each other. Such high-density deployment allows high-throughput usage such as for testing multiple rodent paw guarding simultaneously.

In one embodiment, a method for assaying for an antinociceptive drug is provided. A tag such as described above may be attached to a paw of a rodent. A potential anti-nociceptive drug may then be administered to the rodent. A nociceptive stimulus, such as a formalin injection or a heat source, may be applied to the paw of the rodent and the resulting spontaneous pain in the injured paw is monitored by the above-described system. The system monitors the spontaneous pain by detecting the impedance change induced by the tag, which is dependent on the vertical position of the injured paw.

Although one advantageous application of the systems and methods described herein is for detecting spontaneous pain by the elevation of a rodent paw, it should be recognized that the systems and methods may be used to detect the position of other parts of the rodent, or other laboratory animals. Any behavior that can be characterized by a vertical position change of a portion of a laboratory animal could be monitored in an automated manner with the system described herein. Such behaviors could include various movement disorders, rearing, grooming, scratching, head bobbing/stereotypy, and sexual behaviors. In addition to pain, the methods and devices described herein could be useful in studying disease treatment, pharmacological effects on movement, and mechanisms of action. For monitoring other behaviors, the tag can be attached to a variety of different locations on a laboratory animal including the torso or head, for example. It can be affixed in a variety of ways as well, including with adhesive, a bracelet structure, or implanted under the skin. In some cases, tag motion that is not vertical can be detected. For example, if the inductor of the tag rotates around a horizontal axis, this will be detectable as the plane of the inductor moves with respect to the field lines in the cage. In another embodiment, a tag with three orthogonal LC circuits can be constructed. If three orthogonal pairs of detection coils are placed around the cage aligned along the x-axis, y-axis, and z-axis, then three dimensional position of the tag within the cage can be determined. In this embodiment, it would be advantageous for the three LC circuits on the tag to have different resonant frequencies. This would reduce cross-talk between the coils and make detection more reliable.

EXAMPLE

To induce inflammation, a complete Freund's adjuvant (CFA) was injected into both the ankle and plantar surfaces of the hind paw of rats (0.1 mL in each area). Rats were tested for paw guarding 8 hours post CFA injection using the detectors as described in FIGS. 1 and 2. Spontaneous paw guarding was measured over a period of 5 minutes as cumulative duration (in seconds) during which rats lifted their injured hind paws. This measurement can be made by, for example, sampling the tag height signal (FIG. 2), comparing the signal to a suitable threshold, and characterizing the amount of time the signal is above versus below the threshold. This measurement was repeated twice separated by two intervals of 5 minutes each.

Figure 6B:
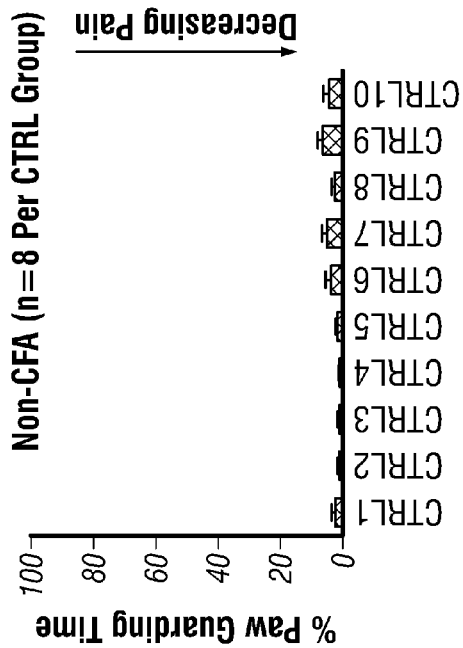
FIGS. 6A-6D are diagrams showing results of experiments monitoring spontaneous pain in an injured paw of a rodent.
Figure 6D:
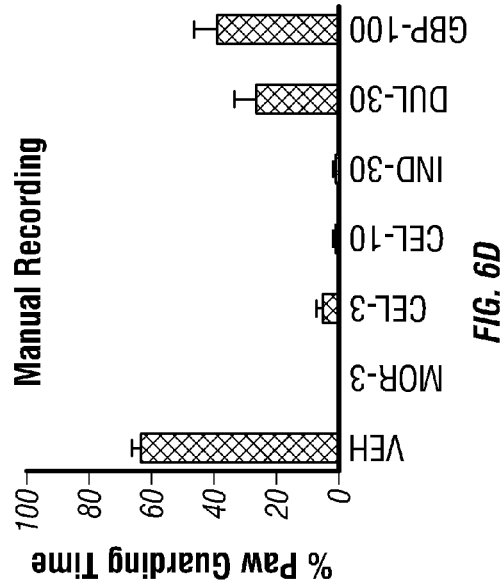
Figure 6A:
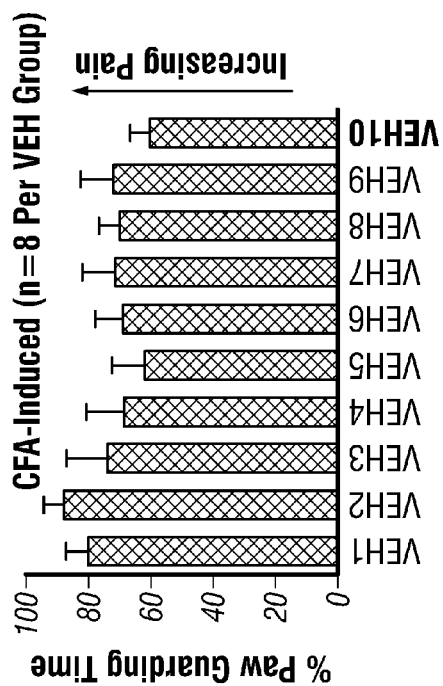

CFA injections induced a dramatic increase in paw guarding (71%±3% mean of 10 independent tests as shown in FIG. 6A) when compared to the control (healthy, non-CFA treated rats) (3.5%±0.4%; mean of 10 independent tests as shown in FIG. 6B).

Figure 6C:
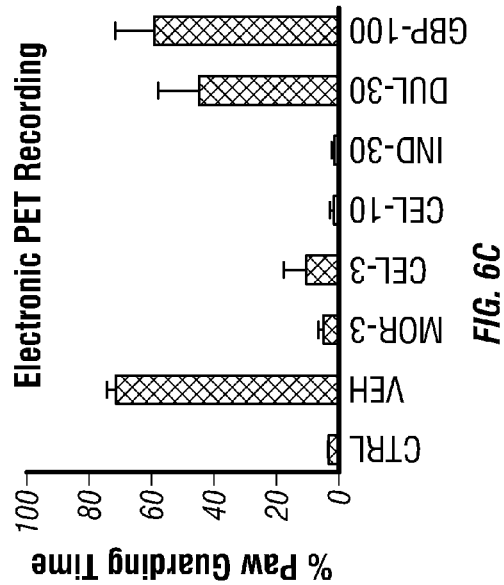

Standard analgesic drugs were tested 8 hours followed CFA injection for their effects on paw guarding. Marketed drugs known to be efficacious showed significant reversal of paw guarding behavior in this model. Morphine, Celebrex, and Indomethacin dramatically reduced paw guarding, while Gabapentin and Duloxetine had a more modest effect (see FIG. 6C). Moreover, results obtained using the instrument described here are compared with manual observation and recording shown in FIG. 6D. FIGS. 6C and 6D show that results obtained manually compare well with those obtained automatically using the instrument.

The foregoing description details certain embodiments of the invention. It will be appreciated, however, that no matter how detailed the foregoing appears in text, the invention may be practiced in many ways. It should be noted that the use of particular terminology when describing certain features or aspects of the invention should not be taken to imply that the terminology is being re-defined herein to be restricted to including any specific characteristics of the features or aspects of the invention with which that terminology is associated.

While the above detailed description has shown, described, and pointed out novel features of the invention as applied to various embodiments, it will be understood that various omissions, substitutions, and changes in the form and details of the device or process illustrated may be made by those skilled in the technology without departing from the spirit of the invention. The scope of the invention is indicated by the appended claims rather than by the foregoing description. All changes which come within the meaning and range of equivalency of the claims are to be embraced within their scope.

What is claimed is:

1. A cage for holding and monitoring a rodent comprising: a bridge of four legs comprising:
    a first coil positioned below a floor of the cage; and
    a second coil positioned above the floor of the cage;
a resonant circuit attached to a portion of a laboratory animal, said resonant circuit defining a resonant frequency;
a signal generator electrically coupled to at least one coil configured to drive the at least one coil with at least a first drive signal comprising a first frequency and a second drive signal comprising a second frequency, wherein the second frequency is more distant from said resonant frequency than the first frequency; and
a detection circuit comprising a differential amplifier electrically coupled to at least one coil and configured to detect an impedance change in said at least one coil between application of said first frequency to said at least one coil and application of said second frequency to said at least one coil, and to generate an output signal representative of resonant circuit position with respect to said at least one coil based at least in part on said impedance change;
wherein the signal generator is coupled to a first and second node of said bridge, the first and second nodes being opposite nodes and wherein the detection circuit is coupled to a third and fourth node of said bridge, the third and fourth nodes being opposite nodes.

2. The cage of claim 1, wherein said first coil, said second coil, and said floor are substantially aligned along a common longitudinal axis.

3. The cage of claim 1, wherein said floor is positioned at approximately a midpoint between said first coil and said second coil.

4. The cage of claim 1, wherein the first coil and the second coil are disposed parallel to the floor.

5. The cage of claim 1, wherein the detection circuit comprises an envelope detector electrically coupled to said differential amplifier.

6. The system of claim 5, wherein the detection circuit comprises a sampling circuit coupled to the envelope detector.

7. The cage of claim 1, wherein said resonant circuit comprises an inductor and a capacitor electrically coupled in parallel.

8. The cage of claim 7, wherein the resonant circuit is mounted to a printed circuit board.

9. The cage of claim 1, wherein the output signal is representative of the vertical position of the resonant circuit above the floor.

10. The cage of claim 1, wherein the first and second coil are wired in series forming two legs of the four legs, and wherein the other two legs of the bridge comprise two resistors, one resistor in each leg.

* * * * *

UNITED STATES PATENT AND TRADEMARK OFFICE
CERTIFICATE OF CORRECTION

| | | |
|---|---|---|
| PATENT NO. | : 8,763,559 B2 | Page 1 of 1 |
| APPLICATION NO. | : 13/777239 | |
| DATED | : July 1, 2014 | |
| INVENTOR(S) | : Philip Salzmann et al. | |

It is certified that error appears in the above-identified patent and that said Letters Patent is hereby corrected as shown below:

In the Claims

At Column 10, line 19, change "system" to --cage--.

Signed and Sealed this
Seventeenth Day of February, 2015

Michelle K. Lee
*Deputy Director of the United States Patent and Trademark Office*